United States Patent
Han et al.

(10) Patent No.: US 9,392,990 B2
(45) Date of Patent: *Jul. 19, 2016

(54) APPARATUS AND METHOD FOR ESTIMATING OBJECT INFORMATION

(71) Applicant: SAMSUNG ELECTRONICS CO., LTD., Suwon-si (KR)

(72) Inventors: Seok Min Han, Seongnam-si (KR); Dong Goo Kang, Suwon-si (KR); Sung Su Kim, Yongin-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 105 days.

This patent is subject to a terminal disclaimer.

(21) Appl. No.: 13/970,672

(22) Filed: Aug. 20, 2013

(65) Prior Publication Data

US 2014/0086386 A1 Mar. 27, 2014

(30) Foreign Application Priority Data

Sep. 21, 2012 (KR) ........................ 10-2012-0104925

(51) Int. Cl.
*A61B 6/00* (2006.01)

(52) U.S. Cl.
CPC .................. *A61B 6/583* (2013.01); *A61B 6/482* (2013.01); *A61B 6/502* (2013.01); *A61B 6/5205* (2013.01); *A61B 6/5217* (2013.01); *A61B 6/5294* (2013.01)

(58) Field of Classification Search
CPC ........ A61B 6/482; A61B 6/502; A61B 6/583; A61B 6/5205; A61B 6/5294

USPC .......... 378/5, 37, 56, 62, 98.9, 132; 382/130; 600/431

See application file for complete search history.

(56) References Cited

U.S. PATENT DOCUMENTS

| 6,501,849 | B1* | 12/2002 | Gupta et al. .................. 382/141 |
| 6,683,934 | B1 | 1/2004 | Zhao et al. |
| 2002/0075997 | A1* | 6/2002 | Unger et al. ................. 378/98.9 |
| 2008/0167552 | A1 | 7/2008 | Bouchevreau et al. |
| 2010/0226475 | A1* | 9/2010 | Smith et al. ..................... 378/37 |
| 2011/0142312 | A1 | 6/2011 | Toth et al. |
| 2011/0150183 | A1 | 6/2011 | Wu et al. |

(Continued)

FOREIGN PATENT DOCUMENTS

| KR | 10-2004-0047561 A | 6/2004 |
| KR | 10-2008-0007623 A | 1/2008 |

(Continued)

OTHER PUBLICATIONS

Communication dated Jan. 7, 2014 issued by the European Patent Office in counterpart European Application No. 13185105.7.

*Primary Examiner* — Glen Kao
(74) *Attorney, Agent, or Firm* — Sughrue Mion, PLLC (57) ABSTRACT

An apparatus and method for estimating object information is provided. The object information estimating apparatus includes a database which stores phantom information obtained by projecting a first energy X-ray on a phantom, an input unit which receives first object information obtained by projecting the first energy X-ray on an analysis object, and which receives information on a thickness of the analysis object, and an estimating unit which estimates second object information based on the phantom information, the first object information, and the information on the thickness.

16 Claims, 8 Drawing Sheets

(56) References Cited

U.S. PATENT DOCUMENTS

2012/0101733 A1\* 4/2012 Han et al. .................. 382/132
2015/0063528 A1\* 3/2015 Han et al. .................... 378/5

FOREIGN PATENT DOCUMENTS

| KR | 10-2011-0055870 A | 5/2011 |
| WO | 2012/015280 A2 | 2/2012 |

\* cited by examiner

APPARATUS AND METHOD FOR ESTIMATING OBJECT INFORMATION

CROSS-REFERENCE TO RELATED APPLICATION

This application claims priority from Korean Patent Application No. 10-2012-0104925, filed on Sep. 21, 2012, in the Korean Intellectual Property Office, the entire disclosure of which is incorporated herein by reference in its entirety.

BACKGROUND

1. Field

Methods and apparatuses consistent with exemplary embodiments relate to an apparatus and method for estimating object information.

2. Description of the Related Art

For quantitative medical imaging or quantitative imaging using a multi-energy X-ray, for example, a dual energy X-ray, components of an object to be photographed, for example, an analysis object, may need to be calculated.

In this procedure, when an analysis object, for example, a human body, is photographed using the multi-energy X-ray, substance isolation may be performed with respect to a plurality of substances of the analysis object based on a combination made in view of a thickness, for example, an amount, and a mixing ratio of each substance. Finding an association between an X-ray image and the combination made in view of the thickness and the mixing ratio of the plurality of substances may be referred to as calibration.

In order to detect substances of the analysis object using an analysis system for performing the calibration, a plurality of pieces of object information regarding the analysis object may be required for each energy level. For example, when a dual-energy X-ray is used, the analysis system may require a low-energy object image and a high-energy object image of the analysis object, for detecting the substances of the analysis object.

SUMMARY

According to exemplary embodiments, there is provided an apparatus for estimating object information, the apparatus including a database which stores phantom information obtained by projecting a first energy X-ray on a phantom, an input unit which receives first object information obtained by projecting the first energy X-ray on an analysis object, and which receives information on a thickness of the analysis object, and an estimating unit which estimates second object information, based on the phantom information, the first object information, and the information on the thickness.

The second object information may include information obtained by projecting a second energy X-ray having an energy level differing from an energy level of the first energy X-ray.

The first object information may include an object image acquired by projecting the first energy X-ray on the analysis object, and an intensity value for each of a plurality of pixels of the object image.

The phantom information may include a phantom image acquired by projecting the first energy X-ray on the phantom, and the estimating unit may detect a first area having the intensity value in the phantom image, detect a second area corresponding to the information on the thickness in the phantom image, detect an intersecting area of the first area and the second area, and estimate the second object information by estimating an intensity value at a second energy level corresponding to the intersecting area.

The information on the thickness may include at least one of a thickness value of the analysis object, and information on an area in which the analysis object is displayed on the phantom image.

The estimating unit may estimate at least one piece of third object information on the analysis object, based on the estimated second object information.

According to another aspect of an exemplary embodiment, there is provided a method of estimating object information using an object information estimating apparatus, the method including receiving first object information obtained by projecting a first energy X-ray on an analysis object, receiving information on a thickness of the analysis object, and estimating second object information based on phantom information stored in a database of the object information estimating apparatus, the first object information, and the information on the thickness.

BRIEF DESCRIPTION OF THE DRAWINGS

The above and other aspects of exemplary embodiments will become apparent and more readily appreciated from the following detailed description of certain exemplary embodiments, taken in conjunction with the accompanying drawings of which.

DETAILED DESCRIPTION OF THE EXEMPLARY EMBODIMENTS

Reference will now be made in detail to exemplary embodiments, examples of which are illustrated in the accompanying drawings, wherein like reference numerals refer to the like elements throughout. Exemplary embodiments are described below in order to explain the present disclosure by referring to the figures.

When it is determined that a detailed description is related to a related known function or configuration which may make the purpose of the present disclosure unnecessarily ambiguous in the description, such detailed description will be omitted. Also, terminologies used herein are defined to appropriately describe the exemplary embodiments and thus may be changed depending on a user, the intent of an operator, or a custom. Accordingly, the terminologies may be defined based on the following overall description of this specification.

Figure 1:
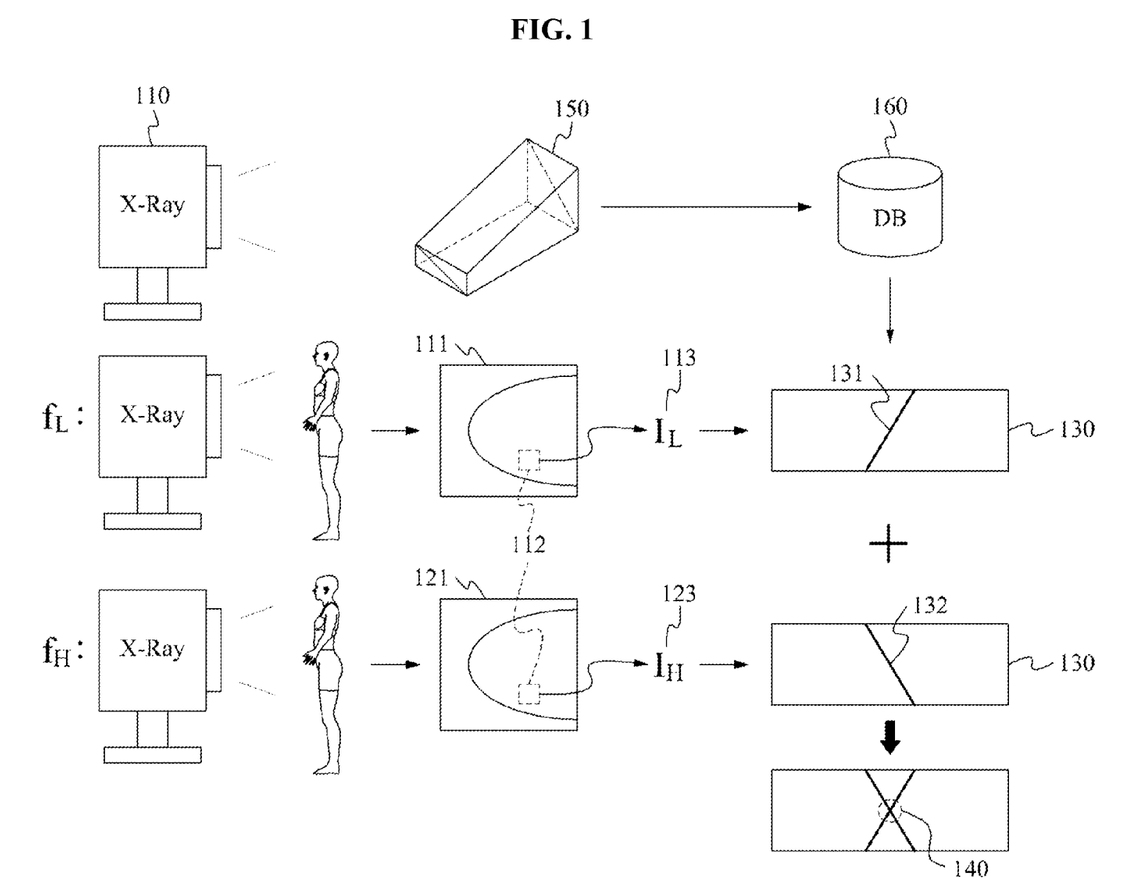
FIG. 1 is a diagram illustrating an analysis system for analyzing components of an analysis object using a multi-energy X-ray.

FIG. 1 is a diagram illustrating an analysis system for analyzing components of an analysis object using a multi-energy X-ray. For example, FIG. 1 illustrates an operation of the analysis system performing calibration.

Referring to FIG. 1, the analysis system may analyze components of an analysis object to be photographed, for example, a body part of a human, and the like. The term "analysis object" may refer to an object to be analyzed. In this instance, the analysis system may use phantom information stored in a database 160, and a low-energy object image 111 and a high-energy object image 121 acquired by projecting a multi-energy X-ray 110 on the analysis object via an X-ray emitting device.

In particular, the analysis system may detect an area 131 having an intensity value IL 113 of a pixel 112 of the low-energy object image 111, in a phantom image 130 acquired by projecting the multi-energy X-ray 110 on a phantom 150. In addition, the analysis system may detect an area 132 having an intensity value IH 123 of a pixel 112 of the high-energy object image 121, in the phantom image 130. According to exemplary embodiments, the analysis system may detect an intersecting area 140 of the two detected areas, and may detect information on a thickness and a mixing ratio of a plurality of substances constituting a part of a phantom corresponding to the detected intersecting area 140. The detected information on the thickness and the mixing ratio may be used as information about substances constituting the analysis object.

Figure 2:
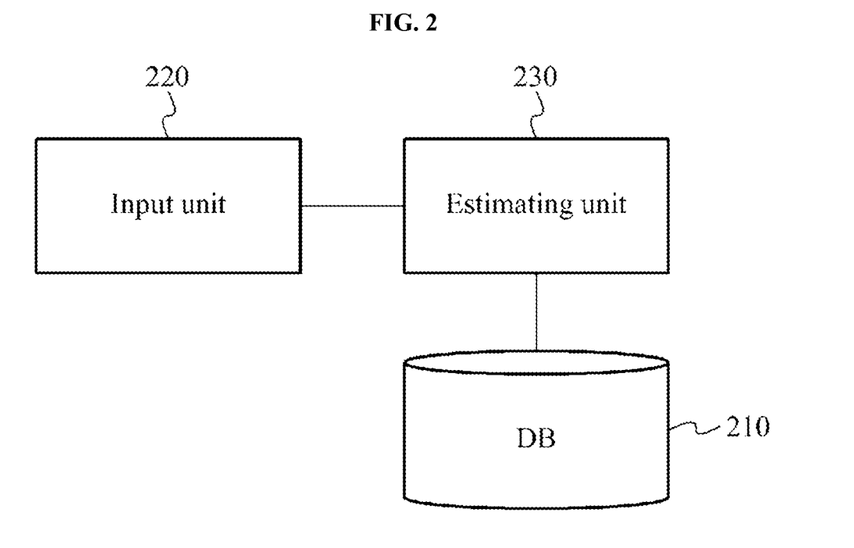
FIG. 2 is a diagram illustrating a configuration of an apparatus for estimating object information according to exemplary embodiments.

FIG. 2 is a diagram illustrating a configuration of an apparatus for estimating object information according to exemplary embodiments.

Referring to FIG. 2, the object information estimating apparatus may include a database 210, an input unit 220, and an estimating unit 230.

The object information estimating apparatus may estimate object information corresponding to an energy level differing from a predetermined energy level, from object information corresponding to the predetermined energy level with respect to an analysis object. For example, the object information estimating apparatus may estimate high-energy object information using low-energy object information, or may estimate low-energy object information using high-energy object information. Accordingly, although the analysis object may be photographed using a single energy level X-ray by the object information estimating apparatus, an effect of obtaining object information corresponding to another energy level may be achieved according to exemplary embodiments.

The object information estimating apparatus may refer to the database 210 in which phantom information is stored, for estimating the object information. The phantom information may include information obtained by projecting a first energy X-ray on a phantom including a plurality of substances. Hereinafter, the phantom and the phantom information will be described with reference to FIGS. 3 and 4.

Figure 3:
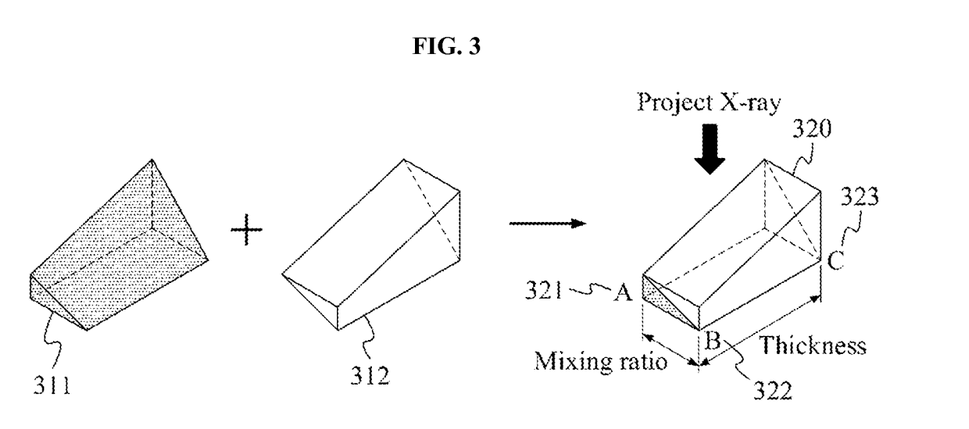
FIG. 3 is a diagram illustrating a phantom according to exemplary embodiments.

FIG. 3 is a diagram illustrating a phantom according to exemplary embodiments.

Referring to FIG. 3, the phantom may be formed of two substances. According to exemplary embodiments, each of the substances constituting the phantom may correspond to one of an adipose tissue and a glandular tissue, although is not limited thereto according to other exemplary embodiments.

The phantom may be manufactured in the form of a trapezoidal shape 320. Accordingly, thicknesses of a first substance 311 and a second substance 312 constituting the phantom may increase in a direction from a front side corresponding to B 322 to a back side corresponding to C 323. For example, the thicknesses of the first substance 311 and the second substance 312 at the front side corresponding to B 322 of the phantom may be 5 centimeters (cm). The thicknesses may increase linearly toward the back side corresponding to C 323, and the thicknesses of the first substance 311 and the second substance 312 at the back side corresponding to C 323 may be 10 cm. It is understood that the thicknesses are not limited to 5 cm ranging up to 10 cm, and many different thicknesses may be used. It is further understood that the phantom may be many different types of shapes other than a trapezoidal shape.

Since the first substance 311 and the second substance 312 may be combined with each other diagonally, a mixing ratio of the first substance 311 to the second substance 312 may increase or decrease linearly in a direction from a left side corresponding to A 321 to a right side corresponding to B 322 of the phantom. For example, the ratio of the first substance 311 to the second substance 312 at the left side corresponding to A 321 of the phantom may be 10:0. The mixing ratio may be changed linearly toward the right side corresponding to B 322, and the mixing ratio of the first substance 311 to the second material 312 at the right side corresponding to B 322 may be 0:10. It is understood that the mixing ratio may also be changed in other than a linear fashion.

According to exemplary embodiments, phantom information may include a phantom image acquired by projecting an X-ray on a phantom. In particular, the phantom image may be acquired by projecting the X-ray on the phantom manufactured as shown in FIG. 3. According to exemplary embodiments, the phantom image may be acquired by projecting the X-ray from an upper direction of the phantom.

Figure 4:
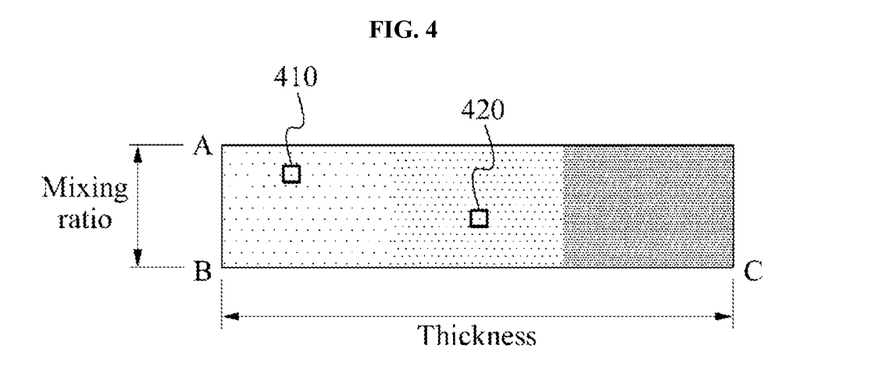
FIG. 4 is a diagram illustrating a phantom image acquired by projecting a single energy X-ray on the phantom of FIG. 3.

FIG. 4 is a diagram illustrating a phantom image acquired by projecting a single energy X-ray on the phantom of FIG. 3.

Since the phantom image may be acquired by projecting the X-ray from an upper direction of the phantom of FIG. 3, the phantom image may be provided in a quadrangular shape. In this instance, each of a plurality of pixels of the phantom image may include information on corresponding thicknesses of the first substance 311 and the second substance 312, and a corresponding mixing ratio of the first substance 311 to the second substance 312.

For example, a first pixel 410 may include information of thicknesses corresponding to 5.5 cm and a mixing ratio of the first substance 311 to the second substance 312 corresponding to 8:2. In addition, a second pixel 420 may include information of thicknesses corresponding to 7.5 cm and a mixing ratio of the first substance 311 to the second substance 312 corresponding to 5:5.

Referring back to FIG. 2, the input unit 220 may receive input first object information obtained by projecting a first energy X-ray on the analysis object. The analysis object may include various targets, for example, a human, an animal, an object, and the like.

The object information may include an object image acquired by projecting the first energy X-ray on the analysis object, and an intensity value for each of a plurality of pixels of the object image.

Figure 5:
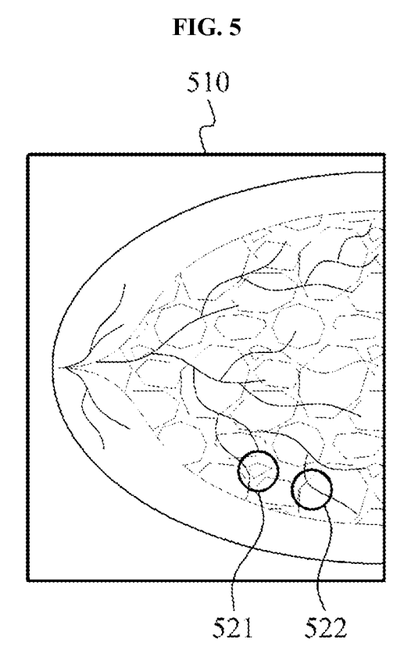
FIG. 5 is a diagram illustrating an object image according to exemplary embodiments.

For example, referring to FIG. 5, the analysis object may correspond to a breast of a human. When the single energy X-ray is projected on the analysis object, object information may include a single energy radiography image 510 of the analysis object, and an intensity value for each pixel of the radiography image 510 of the analysis object. For example, an intensity value for a first pixel 521 may be "10," and an intensity value for a second pixel 522 may be "5."

Figure 6:
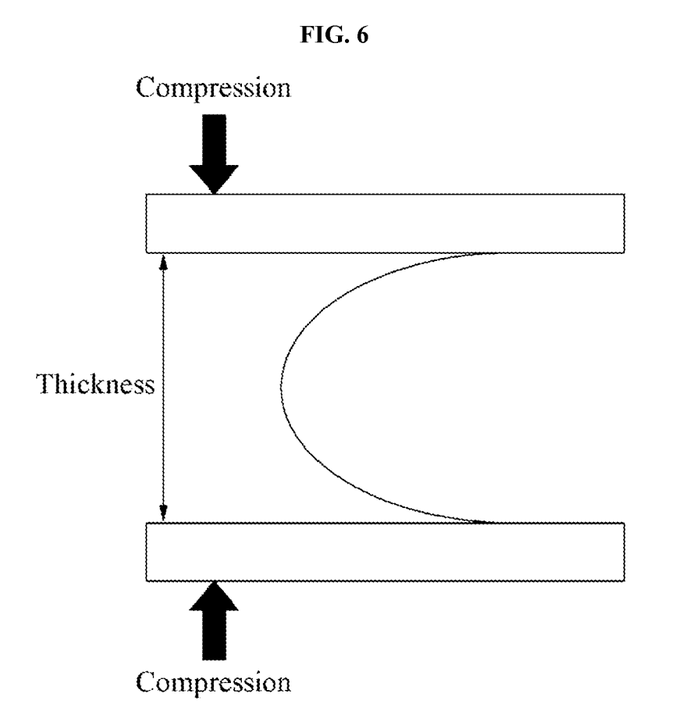
FIG. 6 is a diagram illustrating an operation of acquiring an object image by compressing an analysis object and projecting an X-ray according to exemplary embodiments.

The input unit 220 may receive input information on a thickness of the analysis object. The information on the thickness of the analysis object may include at least one of a thickness value of the analysis object, and information on an area in which the analysis object is displayed on the phantom image. For example, referring to FIG. 6, as a method of obtaining the object information about the analysis object, a method of acquiring an object image by compressing the analysis object with two plates and projecting an X-ray may be used. A thickness value of the analysis object may be determined by measuring a distance between the two plates used to compress the analysis object when an object image is acquired using the method. In addition, in light of experience in photographing an analysis object, an area in which the analysis object is to be displayed on the phantom image may be known in advance. The input unit 220 may receive input information, such as, for example, information on the thickness of the analysis object.

The estimating unit 230 may estimate second object information, based on the phantom information stored in the database 210, the first object information, and the information on the thickness of the analysis object.

The second object information may indicate information obtained by projecting a second energy X-ray having an energy level differing from an energy level of the first energy X-ray. For example, when the energy level of the first energy X-ray is lower than the energy level of the second energy X-ray, information obtained by projecting the second energy X-ray having a higher energy level than the first energy X-ray may correspond to the second object information. In this instance, the first object information may correspond to low-energy object information, and the second object information may correspond to high-energy object information. Conversely, when the energy level of the first energy X-ray is higher than the energy level of the second energy X-ray, information obtained by projecting the second X-ray having a lower energy level than the first energy X-ray may correspond to the second object information. In this instance, the first object information may correspond to high-energy object information, and the second object information may correspond to low-energy object information.

According to exemplary embodiments, the estimating unit 230 may estimate at least one piece of third object information on the analysis object, based on the estimated second object information. For example, in a case in which an energy level increases sequentially in an order of a first energy level, a second energy level, and a third energy level, the estimating unit 230 may estimate the third object information on the analysis object based on the estimated second object information. In this instance, the third object information may correspond to information obtained by projecting an X-ray using the third energy level having a higher energy level than the second energy level. As described above, the estimating unit 230 may perform the operation of estimating object information repeatedly, thereby estimating a plurality of pieces of object information from a single piece of object information. Accordingly, although the analysis object is photographed using a single energy level X-ray by the object information estimating apparatus, object information corresponding to multiple energies may be estimated and thus, an analogous effect of photographing the analysis object using a multi-energy X-ray may be achieved.

Hereinafter, an operation of the object information estimating apparatus which estimates second object information will be described in detail with reference to FIG. 7.

Figure 7:
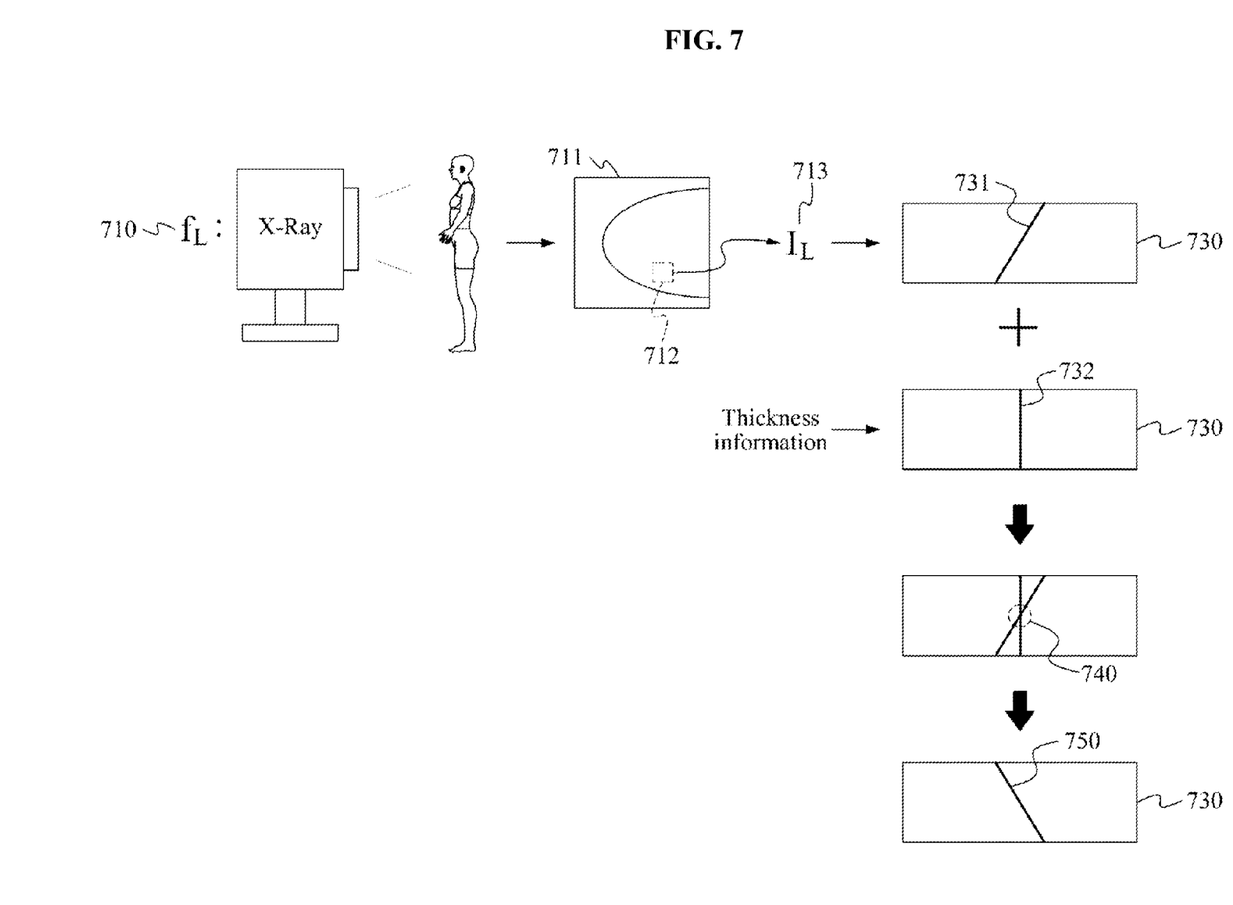
FIG. 7 is a diagram illustrating an operation of estimating second object information by an estimating unit of an apparatus for estimating object information according to exemplary embodiments.

FIG. 7 is a diagram illustrating an operation of estimating second object information by an estimating unit of an apparatus which estimates object information according to exemplary embodiments.

FIG. 7 illustrates an example of an operation of the estimating unit 230 of FIG. 2 which estimates high-energy object information using low-energy object information. However, conversely, an operation of estimating low-energy object information using high-energy object information may be equally applicable.

Referring to FIG. 7, first object information received by the input unit 220 of the object information estimating apparatus of FIG. 2 may include an object image, and an intensity value for each pixel of the object image.

When a low-energy X-ray having a frequency of fL 710 is projected on an analysis object, for example, a breast of a human, a low-energy object image 711 and an intensity value IL 713 for each pixel at that moment may be obtained, and the input unit 220 may receive input of the low-energy object image 711 and the intensity value IL 713. For example, an intensity value for a pixel 712 selected by a user in the analysis object, hereinafter, also referred to as the "selected pixel" 712, may correspond to "10."

In this instance, the estimating unit 230 may detect a first area 731 having the intensity value IL 713 in a phantom image 730 stored in the database 210. For example, when the intensity value IL 713 corresponds to "10," the estimating unit 230 may detect a portion having an intensity value of "10" in the phantom image 730, thereby detecting the first area 731.

In addition, the estimating unit 230 may detect a second area 732 corresponding to information on a thickness of the analysis object in the phantom image 730. For example, when the thickness corresponds to 5 cm, the estimating unit 230 may detect an area having a thickness of 5 cm in the phantom image 730.

Further, the estimating unit 230 may detect an intersecting area 740 in which the first area 731 intersects the second area 732. The estimating unit 230 may estimate second object information, by estimating an intensity value at a second energy level corresponding to the intersecting area 740. In particular, the estimating unit 230 may estimate an intensity value at a high energy level corresponding to the intersecting area 740, and may detect an area 750 having the estimated intensity value at the high energy level in the phantom image 730. In this instance, the area 750 having the intensity value at the high energy level may correspond to the high-energy object information.

Accordingly, the area 750 having the intensity value at the high energy level may be obtained from the low-energy object information, without requiring the operation of projecting a high-energy X-ray, for example, an fH X-ray, on the analysis object.

Figure 8:
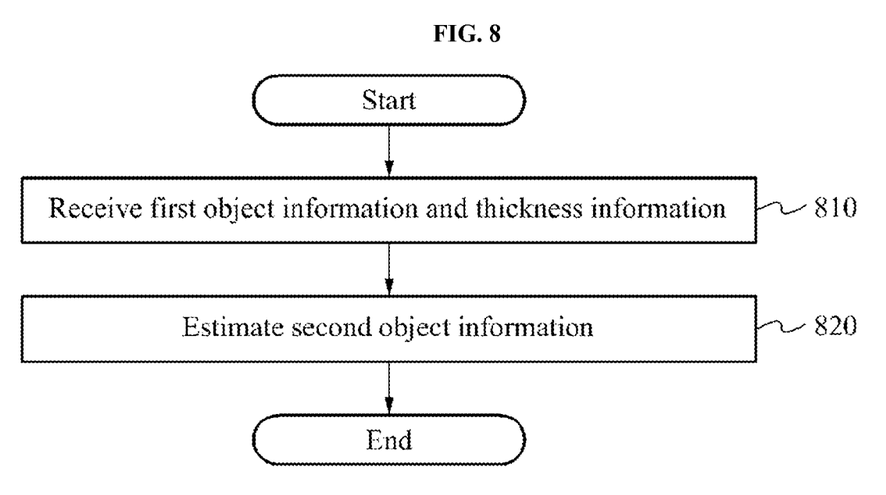
FIG. 8 is a flowchart illustrating a method of estimating object information according to exemplary embodiments.

FIG. 8 is a flowchart illustrating a method of estimating object information according to exemplary embodiments.

Referring to FIG. 8, in the object information estimating method according to exemplary embodiments, object information corresponding to an energy level differing from a predetermined energy level may be estimated from object information corresponding to the predetermined energy level with respect to an analysis object. For example, in the object information estimating method according to exemplary embodiments, high-energy object information may be estimated using low-energy object information, and conversely, low-energy object information may be estimated using high-energy object information. Accordingly, although the analysis object is photographed using a single energy level X-ray by the object information estimating method, an effect of obtaining object information corresponding to another energy level may be achieved according to exemplary embodiments.

In operation 810, first object information obtained by projecting a first energy X-ray on an analysis object, and information on a thickness of the analysis object, may be received. According to exemplary embodiments, the analysis object may include various targets, for example, a human, an animal, an object, and the like.

The object information may include an object image acquired by projecting the first energy X-ray on the analysis object, and an intensity value for each of a plurality of pixels of the object image.

The information on the thickness of the analysis object may include at least one of a thickness value of the analysis object, and information on an area in which the analysis object is displayed on a phantom image.

In operation 820, second object information may be estimated, based on phantom information stored in a database, the first object information, and the information on the thickness of the analysis object.

The second object information may indicate information obtained by projecting a second energy X-ray having an energy level differing from an energy level of the first energy X-ray.

In the object information estimating method according to exemplary embodiments, at least one piece of third object information with respect to the analysis object may be estimated based on the estimated second object information.

According to exemplary embodiments, a first area having an intensity value for each of a plurality of pixels of the object image included in the first object information may be detected in the phantom image included in the phantom information. In addition, a second area corresponding to the information on the thickness of the analysis object may be detected in the phantom image. Further, an intersecting area of the first area and the second area may be detected. Also, second object information may be estimated by estimating an intensity value at a second energy level corresponding to the intersecting area. In particular, in the object information estimating method according to exemplary embodiments, an intensity value at the second energy level corresponding to the intersecting area may be estimated, and an area having the estimated intensity value at the second energy level may be detected in the phantom image. In this instance, the area having the intensity value at the second energy level may correspond to the second object information.

According to exemplary embodiments, although the analysis object is photographed using a single energy level X-ray, an object image at another energy level may be acquired. For example, a high-energy image may be acquired from a low-energy image of the analysis object, and conversely, a low-energy image may be acquired from a high-energy image of the analysis object.

The object information estimating method according to the above-described exemplary embodiments may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments, or vice versa.

Although a few exemplary embodiments have been shown and described, exemplary embodiments are not limited thereto. Instead, it would be appreciated by those skilled in the art that changes may be made to these exemplary embodiments without departing from the principles and spirit of the disclosure, the scope of which is defined by the claims and their equivalents.

What is claimed is:

1. An apparatus for estimating object information, the apparatus comprising:
   a database which stores phantom information obtained by projecting a first energy X-ray on a phantom, the phantom information comprising a phantom image acquired by projecting the first energy X-ray on a phantom;
   an input unit which receives first object information obtained by projecting the first energy X-ray on an analysis object, and which receives information on a thickness of the analysis object, the first object information comprising an object image acquired by projecting the first energy X-ray on the analysis object and an intensity value for each of a plurality of pixels of the object image; and
   an estimating unit which estimates second object information based on the phantom information, the first object information, and the information on the thickness,
   wherein the second object information comprises information obtained by projecting a second energy x-ray, having an energy level differing from an energy level of the first energy X-ray on the analysis object.

2. The apparatus of claim 1, wherein
   the estimating unit detects a first area having the intensity value in the phantom image, detects a second area corresponding to the information on the thickness in the phantom image, detects an intersecting area of the first area and the second area, and estimates the second object information by estimating an intensity value at a second energy level corresponding to the intersecting area.

3. The apparatus of claim 1, wherein the information on the thickness comprises at least one of a thickness value of the analysis object, and information on an area in which the analysis object is displayed on the phantom image.

4. The apparatus of claim 1, wherein the estimating unit estimates at least one piece of third object information on the analysis object, based on the estimated second object information.

5. The apparatus of claim 1, wherein the phantom comprises a trapezoidal shape.

6. The apparatus of claim 1, wherein the phantom comprises a plurality of substances.

7. The apparatus of claim 6, wherein the plurality of substances comprise a first substance corresponding to an adipose tissue and a second substance corresponding to a glandular tissue.

8. The apparatus of claim 6, wherein thicknesses of the plurality of substances increase in a direction from a front side of the phantom at which the first energy X-ray is received to a back side opposite the front side.

9. A method of estimating object information using an object information estimating apparatus, the method comprising:
   receiving first object information obtained by projecting a first energy X-ray on an analysis object, the first object information comprising an object image acquired by projecting the first energy X-ray on the analysis object and an intensity value for each of a plurality of pixels of the object image;

receiving information on a thickness of the analysis object; and estimating second object information based on phantom information stored in a database of the object information estimating apparatus, the first object information, and the information on the thickness, the phantom information comprising a phantom image acquired by projecting the first energy X-ray on a phantom;

wherein the second object information comprises information obtained by projecting a second energy X-ray, having an energy level differing from an energy level of the first energy X-ray, on the analysis object.

10. The method of claim 9, wherein the estimating comprises:

detecting a first area having the intensity value in a phantom image included in the phantom information;

detecting a second area corresponding to the information on the thickness in the phantom image;

detecting an intersecting area of the first area and the second area; and estimating the second object information by estimating an intensity value at a second energy level corresponding to the intersecting area.

11. A non-transitory computer-readable medium comprising a program for causing a computer to perform the operations of:

receiving first object information obtained by projecting a first energy X-ray on an analysis object, the first object information comprising an object image acquired by projecting the first energy X-ray on the analysis object and an intensity value for each of a plurality of pixels of the object image;

receiving information on a thickness of the analysis object; and estimating second object information based on phantom information stored in a database of an object information estimating apparatus, the first object information, and the information on the thickness, the phantom information comprising a phantom image acquired by projecting the first energy X-ray on a phantom;

wherein the second object comprises information obtained by projecting a second energy X-ray, having an energy level differing from an energy level of the first energy X-ray, on the analysis object.

12. An apparatus to analyze an object, the apparatus comprising:

an X-ray emitter which emits a first X-ray on the object to obtain first object information of the object, the first X-ray having a first energy level; and an estimator which estimates second object information of the object based on the first object information and phantom information obtained by emitting the first X-ray on a phantom, the phantom information comprising a phantom image acquired by projecting the first energy X-ray on the phantom, wherein the second object information corresponds to information of the object which is obtainable using a second X-ray having a second energy level different from the first energy level, wherein the first object information comprises an image of the object acquired by projecting the first X-ray on the object at the first energy level, and intensity values of pixels of the image of the object at the first energy level, and wherein the estimator further estimates the second object information based on a thickness of the object.

13. The apparatus of claim 12, wherein the second object information comprise an image of the object at the second energy level, and intensity values of pixels of the image of the object at the second energy level.

14. The apparatus of claim 12, further comprising a database which stores the phantom information.

15. The apparatus of claim 12, wherein the estimating unit further estimates third object information on the object, based on the estimated second object information.

16. The apparatus of claim 12, wherein the phantom comprises a plurality of substances.

* * * * *